United States Patent [19]
Chen et al.

[11] Patent Number: 5,160,339
[45] Date of Patent: Nov. 3, 1992

[54] ENDOSCOPIC SUTURE CLIP

[75] Inventors: Chao C. Chen, Edison; William Zwaskis, Fanwood, both of N.J.; Mark Ortiz, Milford, Ohio

[73] Assignee: Ethicon, Inc., Somerville, Ohio

[21] Appl. No.: 717,134

[22] Filed: Jun. 18, 1991

[51] Int. Cl.⁵ .............................................. A61B 17/00
[52] U.S. Cl. .................................. 606/158; 606/157; 227/902
[58] Field of Search ....................... 606/157, 158, 151; 227/902

[56] References Cited

U.S. PATENT DOCUMENTS

| | | | |
|---|---|---|---|
| 3,753,438 | 8/1973 | Wood et al. | 606/232 |
| 3,874,042 | 4/1975 | Eddleman et al. | 606/157 |
| 4,291,698 | 9/1981 | Fuchs et al. | 606/232 |
| 4,346,869 | 8/1982 | MacNeill | 606/157 |
| 4,418,694 | 12/1983 | Beroff et al. | 606/158 |
| 4,476,865 | 10/1984 | Failla et al. | 606/158 |
| 4,976,722 | 12/1990 | Failla | 606/158 |

FOREIGN PATENT DOCUMENTS 1188946  6/1985  Canada .

Primary Examiner—Stephen C. Pellegrino
Assistant Examiner—Gary Jackson
Attorney, Agent, or Firm—Matthew S. Goodwin

[57] ABSTRACT

An improved surgical clip having first and second leg members joined at their proximal ends by resilient hinge means and terminating at their distal ends in latch means. Each leg member has an outer surface and a clamping inner surface. The outer surface of each leg member is configured to be accepted by the jaws of a clip applier. The improvement in the clip design specifically relates to the design of the clamping inner surface of each leg member of the clip. The clamping inner surface of the first leg member has a convex radius of curvature extending transversely across at least a portion of the width of the first leg member, and the clamping inner surface of the second leg member has a concave radius of curvature extending transversely across at least a portion of the width of the second leg member. The radius of curvature of the clamping inner surface of the first leg member is smaller than, and complementary to, the radius of curvature of the clamping inner surface of the second leg member.

3 Claims, 3 Drawing Sheets

ENDOSCOPIC SUTURE CLIP

BACKGROUND OF THE INVENTION

This invention relates generally to a surgical clip. More particularly, it relates to such a clip suitably adapted to replace a suture knot during endoscopic surgery.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid o specialized instrumentation designed to fit through additional cannulas providing small diameter openings into the desired body cavity as may be required.

An age-old procedure which surgeons are required to perform to repair or reconstruct traumatized bodily tissue is suturing. Fortunately, medical instruments have been recently designed to allow a surgeon to manipulate a suture, or suture and needle combination, through the small diameter opening of a cannula. However, the ability to tie an appropriately placed suture knot has become troublesome and problematical Therefore, in response to this problem, surgeons have sought alternatives to conventional knot-tying techniques which would be suitable during endoscopic surgery. Among these alternatives include the use of hemostatic clips, which are designed to ligate blood vessels and other tubular members, to replace suture knots. Such hemostatic clips are described, for example, in U.S. Pat. Nos. 4,418,694 and 4,476,865. These clips can be readily applied with a clip applier which is designed to function through the small opening of a cannula. Unfortunately, the force required to displace these clips from the suture is inadequately low. As a result, hemostatic clips of the type shown in the art are unsuitable for general endoscopic surgery needs.

In view of the deficiencies of the prior art for creating a useful alternative to tying a suture knot, what is desired within the medical community is a device suitable for application using endoscopic techniques which can successfully replace the suture knot. More specifically, what is needed is a clip particularly adapted for replacing a suture knot during endoscopic surgery, and which exhibits adequate clamping force to function effectively.

BRIEF DESCRIPTION OF THE DRAWINGS

The present invention will be described in greater detail in conjunction with the accompanying drawings wherein.

SUMMARY OF THE INVENTION

The invention is an improved surgical clip. The clip is of the type comprising first and second leg members joined at their proximal ends by resilient hinge means and terminating at their distal ends in latch means. Each leg member has an outer surface and a clamping inner surface. The clamping inner surface is disposed in opposition to the clamping inner surface of the other leg member. The outer surface of each leg member is configured to be accepted by the jaws of a clip applier.

The improvement in the clip design specifically relates to the clamping inner surfaces of the first and second leg members. The clamping inner surface of the first leg member has a convex radius of curvature extending transversely across at least a portion of the width of the first leg member. The clamping inner surface of the second leg member has a concave radius of curvature extending transversely across at least a portion of the width of the second leg member. The radius of curvature of the clamping inner surface of the first leg member is smaller than the radius of curvature of the clamping inner surface of the second leg member. Additionally, the radius of curvature of the clamping inner surfaces of the first and second leg members are complementary so as to minimize the gap which is created between the clamping inner surfaces when the clip is in a clamped position.

The clip of ths invention is particularly adapted to act as a knot clip in those applications requiring the replacement of a suture knot during endoscopic surgery. The clip, when clamped about a suture, exhibits a clamping force significantly greater than the clamping force exhibited by conventional clips disclosed in the art. This significantly increased clamping force allows the clip to function effectively for the application relating to the replacement of a suture knot. Additionally, the clip can be used for other applications, particularly those applications related to endoscopic surgery.

DESCRIPTION OF THE PREFERRED EMBODIMENTS

Figure 1:
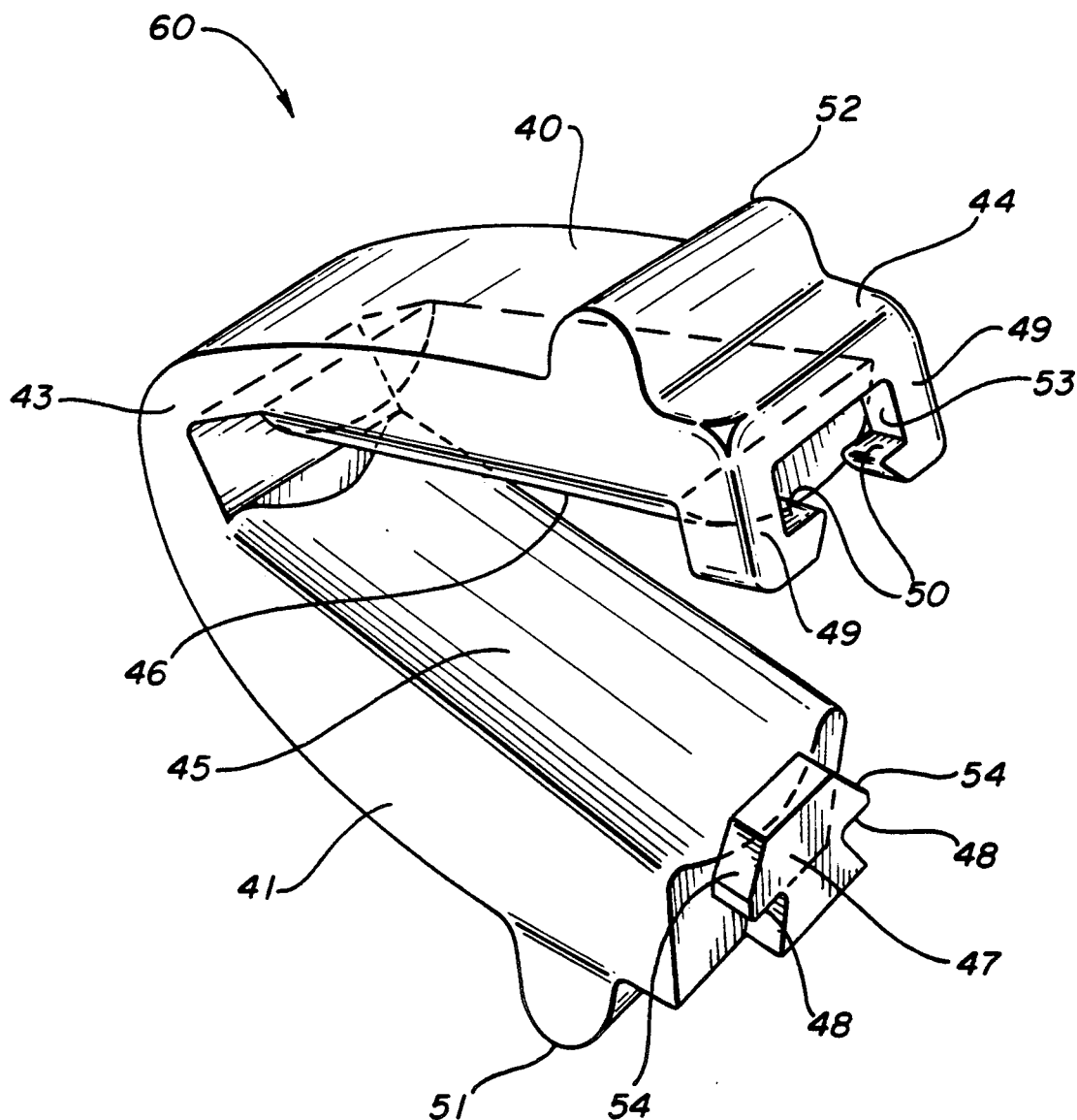
FIG. 1 is a greatly enlarged view in perspective of a clip in accordance with the present invention.

Referring to FIG. 1, there is shown a surgical clip 60 of the present invention. The clip has first and second leg members 40 and 41, respectively. The leg members are connected at their proximal ends by a hinge section 43. The hinge section according to the present invention is resilient; i.e., it has elastic memory and acts as a spring which assists in the packaging of the clip as well as the handling and placement of the clip. First leg member 40 terminates at its distal end in a hook member 44. Hook member 44 has two opposed arms 49 extending perpendicularly from first leg member 40. Each opposed arm 49 terminates with a protrusion means 50, which is disposed perpendicularly from arm 49 and lying substantially in the same plane as that of leg member 40. Each protrusion means 50 has a beveled protrusion end surface 53 to assist in deflecting the arms of the clip when the clip is closed. The second leg member 41 terminates at its distal end in latch member 47. Latch member 47 has two shoulder regions 48 with beveled regions 54 complementary to beveled protrusion end surfaces 53 so as to assist in the deflection of the arms 49 when the clip is closed.

First leg member 40 has a clamping inner surface 46 which has a convex radius of curvature extending transversely and uniformly across the width of first leg member 40. The second leg member 41 has a clamping inner surface 45 which has a concave radius of curvature extending transversely and uniformly across the width of second leg member 41. Preferably, the radius of curvature of clamping surface 45 is smaller than, and complementary to, the radius of curvature of clamping surface 46. Ideally, the radii of curvature for the respective clamping surfaces of the leg members are configured to minimize the gap between the clamping surfaces which forms when the clip is in a clamped position. Although the particular embodiment shown in FIGS. 1-3 has the radius of curvature extending transversely across the entire width of the leg member, the radius of curvature may extend across only a portion of the width of the leg member if there is a corresponding increase in the radius of curvature over that portion of the leg member which is curved.

Figure 2:
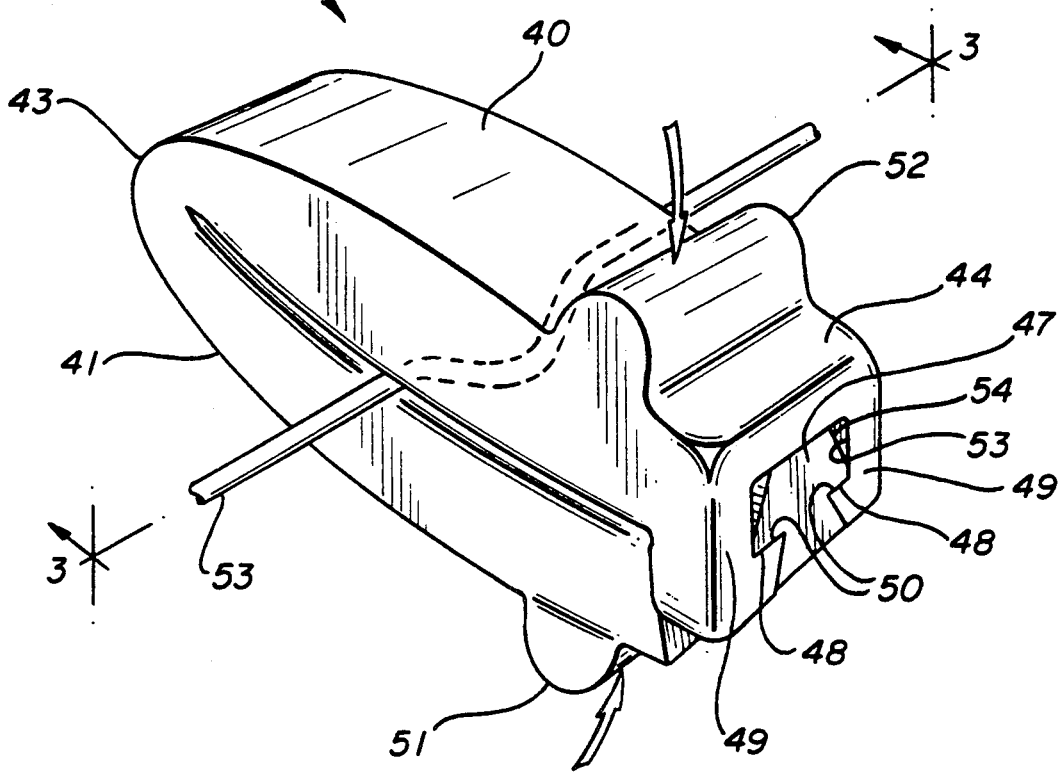
FIG. 2 illustrates the clip of FIG. 1 clamped about a suture.

Disposed on the outer surface of each leg member are cylindrical bosses 51 and 52 to manipulate the clip in a suitable clip applier, preferably an endoscopic clip applier. Referring now to FIGS. 1 and 2, a suture can be clamped by urging leg members 40 and 41 toward each other by applying force in the direction of the arrows at cylindrical bosses 51 and 52. As force is applied, shoulder end regions 54 contact protrusion end surfaces 53 and deflect arms 49 of hook member 44 as the two leg members are pivoted about the resilient hinge 43 and closed about a suture 53. Closure is complete when shoulder regions 48 are disposed in tight contact on top of protrusion means 50 so as to firmly lock latch member 47 within hook member 44.

Figure 3:
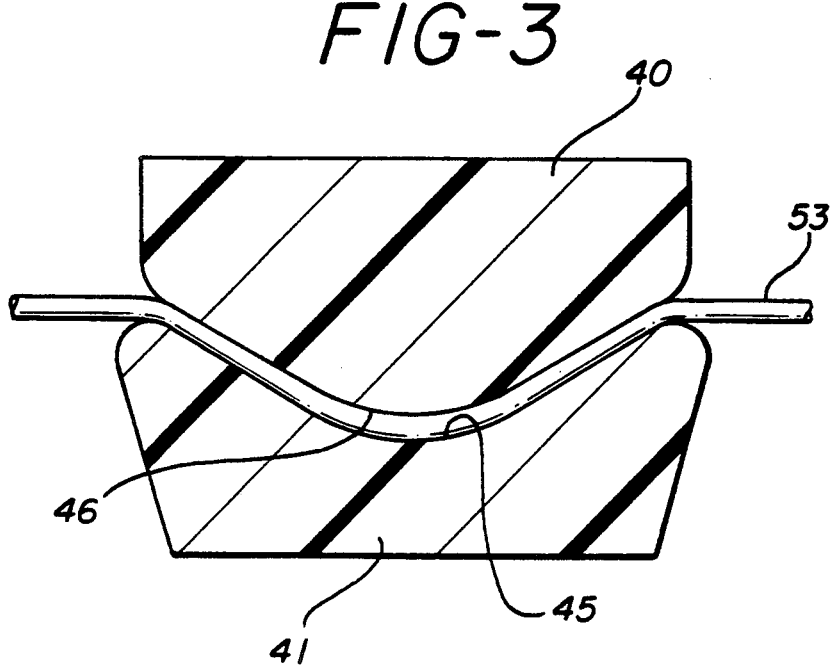
FIG. 3 is a cross-sectional view taken along line 5—5 of FIG. 2.

As is clearly shown in the cross-sectional view of FIG. 3, suture 53 conforms to the radii of curvature of complementary clamping surfaces 45 and 46, thereby being crimped within the clip. This crimped suture configuration advantageously increases the length of suture 53 which is securely clamped by the clip. Therefore, the pull force required to disengage suture 53 from the clip increases significantly.

Figure 4:
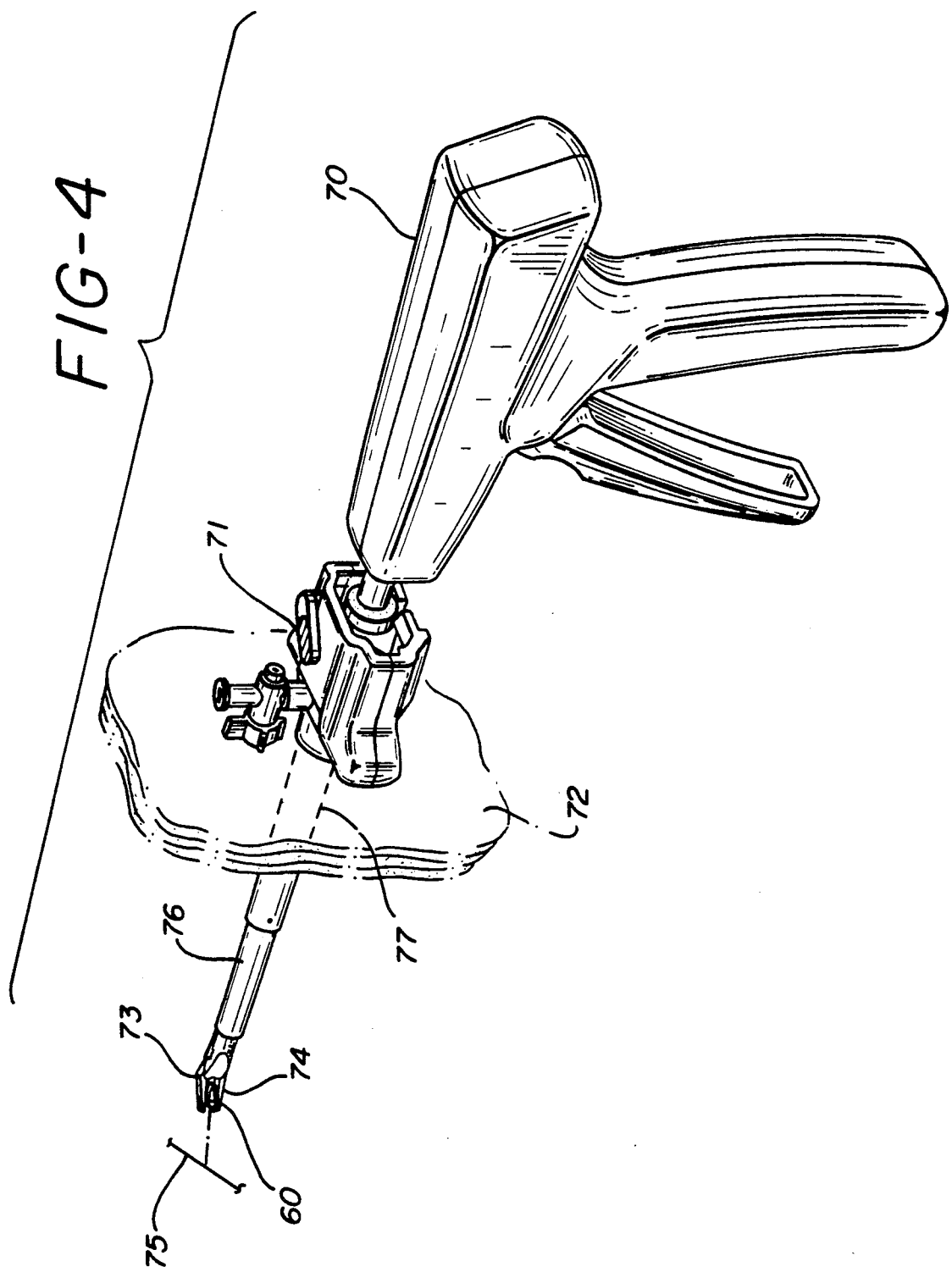
FIG. 4 illustrates an endoscopic clip applier for endoscopically clamping a suture with a clip of this invention.

The clips within the scope of the present invention are suitably adapted for endoscopic applications to replace a conventional suture knot. This can be accomplished as illustrated in FIG. 4. Referring now to FIG. 6, there is shown a clip applier 70 having a long, small-diameter longitudinal member 76. Longitudinal member 76 is adapted to be inserted into a conventional trocar 71 through trocar cannula 77. The trocar is used to provide an opening through bodily tissue 72 for access to the surgical site. The clip applier 70 has jaws 73 at its distal end which are configured in such a manner as to facilitate grasping the outer surface of the legs of the clip 74. Clip applier 70 is maneuvered within the surgical site to place clip 74 about suture 75 which is to be clamped.

The clips of the invention can be made of any biocompatible material using conventional fabrication methods. The clips can be composed of various biocompatible metals, e.g. titanium and tantalum, and polymeric materials. Preferably, the clips are made of bioabsorbable polymeric materials such as homopolymers and copolymers of glycolide, lactide and para-dioxanone. The preferred means for fabricating clips from bioabsorbable polymeric materials is to inject a suitable polymer melt into an appropriately designed mold at process conditions conventionally employed for such polymer systems. After the polymer melt cools, the molded polymer shaped in the mold to meet the design criteria of the clip can be readily released from the mold. The molded clip can then be sterilized using conventional methods to render the clip suitable for surgical applications.

The description of this preferred embodiment should not be construed in any way to limit the scope of the claimed invention. Numerous additional embodiments within the scope and spirit of the invention will become readily apparent to those skilled in the art.

We claim:

1. A surgical clip comprising first and second leg members joined at their proximal ends by resilient hinge means and terminating at their distal ends in latch means, each leg member having an outer surface and a clamping inner surface, said clamping inner surface being in opposition to the clamping inner surface of the other leg member, the outer surface of each leg member being configured to be accepted by the jaws of a clip applier;

the improvement wherein the clamping inner surface of said first leg member has a convex radius of curvature extending transversely across substantially the entire width of said first leg member, the clamping inner surface of said second leg member has a concave radius of curvature extending transversely across substantially the entire width of said second leg member, the radius of curvature of the clamping inner surface of said first leg member being smaller than the radius of curvature of the clamping inner surface of said second leg member, the radius of curvature of the clamping inner surfaces of said first and second leg members being complementary, and when the clip is in a clamped position, the clamping inner surfaces of said first and second leg members are in substantially complete contacting relationship so as to minimize the gap which is created between said surfaces.

2. The clip of claim 1 wherein said radii of curvature of the clamping inner surfaces of said first and second leg members are uniform.

3. The clip of claim 2 wherein the outer surface of each leg member includes a cylindrical boss to facilitate engagement of said clip by the jaws of a clip applier.

* * * * *